United States Patent [19]

Bernáth et al.

[11] Patent Number: 4,622,329
[45] Date of Patent: Nov. 11, 1986

[54] 1-CYCLOHEXYL-3,4-DIHYDROISOQUINO-LINE DERIVATIVES AND PHARMACEUTICAL COMPOSITIONS CONTAINING THEM

[75] Inventors: Gábor Bernáth; Jenó Kóbor; János Lázár; Gábor Motika, all of Szeged; Elemer Ezer, Budapest; György Hajós, Budapest; Éva Pálosi, Budapest; László Dénes, Budapest; László Szporny, Budapest, all of Hungary

[73] Assignee: Richter Gedeon Vegyeszeti Gyart R.T., Budapest, Hungary

[21] Appl. No.: 721,880

[22] Filed: Apr. 10, 1985

[30] Foreign Application Priority Data

Apr. 11, 1984 [HU] Hungary ............................. 1393/84

[51] Int. Cl.$^4$ ..................... A61K 31/47; C07D 217/16
[52] U.S. Cl. .................................. 514/307; 546/145; 546/146; 546/147
[58] Field of Search ....................... 546/146, 145, 147; 514/307

[56] References Cited

PUBLICATIONS

Lucas, *Organic Chemistry*, Sec. Ed., 1953, American Book Co., New York, pp. 412–413.

*Primary Examiner*—Glennon H. Hollrah
*Assistant Examiner*—James H. Turnipseed
*Attorney, Agent, or Firm*—Keil & Weinkauf

[57] ABSTRACT

The invention relates to new 1-cyclohexyl-3,4-dihydroisoquinoline derivatives of the formula (I)

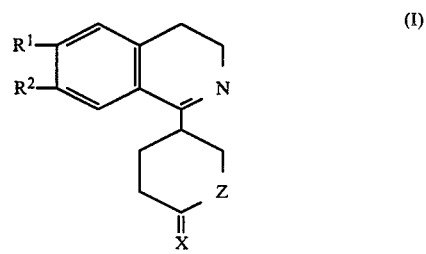

wherein $R^1$ and $R^2$ each independently represents hydrogen, hydroxyl or alkoxy having from 1 to 6 carbon atoms, X is oxygen and Z is a $=CH_2$ or $=CH-COOR^3$ group, in which $R^3$ is hydrogen or alkyl having from 1 to 6 carbon atoms; or X represents an $=NR^4$ group, in which $R^4$ is hydrogen or hydroxyl, and Z is a $=CH-CN$, $=CH_2$ or $=CH-COOR^3$ group, in which $R^3$ is as defined above, and acid addition salts thereof.

The compounds of formula (I) are pharmaceutically active, in particular show antispasm, analgesic, gastric acid secretion inhibiting, sedative and hypnotic activity and effectively reduce the alcoholic narcosis time. According to a further aspect of the invention there is provided a process for the preparation of these compounds. The invention further relates to pharmaceutical compositions containing them as active ingredient.

5 Claims, No Drawings

1-CYCLOHEXYL-3,4-DIHYDROISOQUINOLINE DERIVATIVES AND PHARMACEUTICAL COMPOSITIONS CONTAINING THEM

The invention relates to new 1-cyclohexyl-3,4-dihydroisoquinoline derivatives, a process for their preparation and pharmaceutical compositions containing them as active ingredient. More particularly, the invention concerns new 1-cyclohexyl-3,4-dihydroisoquinoline derivatives of the formula (I)

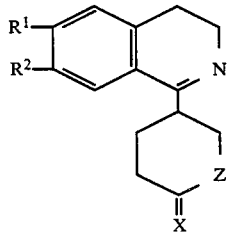

wherein
$R^1$ and $R^2$ each independently represents hydrogen, hydroxyl or alkoxy having from 1 to 6 carbon atoms,
X is oxygen and
Z is a $=CH_2$ or $=CH-COOR^3$ group, in which $R^3$ is hydrogen or alkyl having from 1 to 6 carbon atoms; or
X represents an $=NR^4$ group, in which $R^4$ is hydrogen or hydroxyl, and
Z is a $=CH-CN$, $=CH_2$ or $=CH-COOR^3$ group, in which $R^3$ is as defined above,
and acid addition salts thereof.

In the compounds of formula (I) the alkyl groups as such or as parts of other groups are straight-chained or branched saturated hydrocarbon groups having from 1 to 6 carbon atoms, e.g. methyl, ethyl, n-propyl, isopropyl, n-butyl, isobutyl, tert.-butyl, n-pentyl, isopentyl, n-hexyl or isohexyl groups.

According to the invention compounds of the formula (I), wherein $R^1$, $R^2$, X, Z, $R^3$ and $R^4$ are as defined above, and acid addition salts thereof are prepared by (a) cyclizing a heptane-dicarboxylic acid derivative of the formula (II),

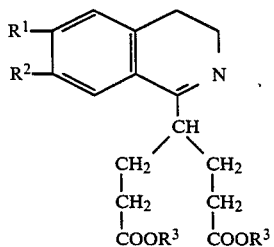

wherein $R^1$ and $R^2$ are as defined above and $R^3$ is a $C_{1-6}$-alkyl group, in the presence of an alkali metal, alkali metal alcoholate or amide, to yield compounds of the formula (I), in which X is oxygen, Z is a $=CH-COOR^3$ group and $R^3$ is alkyl having from 1 to 6 carbon atoms, while $R^1$ and $R^2$ have the same meanings as defined above, or (b) cyclizing a heptane-dicarboxylic acid dinitrile derivative of the formula (III),

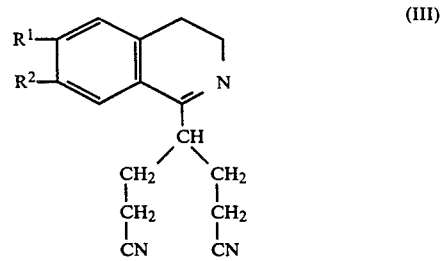

wherein $R^1$ and $R^2$ are as defined above, in the presence of an alkali metal, alkali metal alcoholate or amide, to yield compounds of the formula (I), in which X is an $=NH$ group, Z is a $=CH-CN$ group, and $R^1$ and $R^2$ are as defined above, and if desired, subjecting a compound of the formula (I) obtained in process variant (a), wherein X, Z, $R^1$, $R^2$ and $R^3$ are as defined in connection with process variant (a), to hydrolysis and/or decarboxylation, and/or, if desired, reacting a compound of the formula (I), in which X is oxygen, Z, $R^1$, $R^2$ and $R^3$ are as defined above, with hydroxyl amine or ammonia to yield a corresponding compound of the formula (I), in which X is an $=NR^4$ group, wherein $R^4$ is as defined above, and/or, if desired, in a compound of formula (I) converting a group $R^1$ and/or $R^2$ into another group within the definition of $R^1$ and $R^2$, respectively, and/or, if desired, converting a compound of the formula (I) to an acid addition salt thereof.

The compounds of the formula (I) are pharmaceutically active, in particular show antispasm, analgesic, gastric acid secretion inhibiting, sedative and hypnotic activity and effectively reduce the alcoholic narcosis time.

According to a further aspect of the invention there are provided pharmaceutical compositions comprising, as active ingredient, at least one compound of formula (I) as hereinabove defined, or a physiologically compatible acid addition salt thereof, in association with a pharmaceutical carrier or excipient.

There are numerous pharmaceutically active isoquinoline derivatives known in the art [see e.g. Ehrhart-Ruschig, Arzneimittel, S. Ebel: Synthetische Arzneimittel, Verlag Chemie]. The isoquinoline derivatives, however, in which a cyclohexyl group is attached to the 1-position of the isoquinoline ring are structurally completely new, and there is nothing in the prior art which would suggest that these or structurally closely related compounds would have valuable pharmaceutical properties.

Of the starting compounds having the formulae (II) and (III) those in which $R^1$ and $R^2$ both represent hydrogen are known [S. G. Agalyan, L. A. Nersosyun, and Zs. A. Hanamiryan: Arm. Chim. Zsurn. 20, 45 (1967)], and can for example be prepared from the corresponding 1-methylisoquinoline derivatives. The other compounds of the formulae (II) and (III) (in which $R^1$ and/or $R^2$ have other meanings) can be prepared by conventional reactions known in the art.

Starting from the compounds of formula (II), compounds of the formula (I), in which X is oxygen, Z stands for a $=CH-COOR^3$ group and $R^3$ is alkyl having from 1 to 6 carbon atoms (process a)) can be prepared under the conditions of Claisen condensation.

More particularly, the diesters of the formula (II) may be cyclized in the presence of an alkali metal, alkali metal alcoholate or amide to yield the corresponding compounds of formula (I) under splitting off of alcohol. Preferably sodium methylate or ethylate is used to facilitate the ester condensation but the reaction may be performed also in the presence of sodium metal or sodium amide. The reaction is carried out in a solvent inert under the reaction conditions, preferably an aromatic organic solvent, such as benzene or toluene, at elevated temperature, preferably under reflux.

Process variant (b) can be accomplished essentially under the same reaction conditions as process variant (a), i.e. in the presence of an alkali metal, alkali metal alcoholate or amide, preferably sodium, sodium ethylate or methylate or sodium amide, most preferably sodium methylate or ethylate, in an organic solvent inert under the reaction conditions, at elevated temperature, preferably under reflux. As a solvent preferably aromatic organic solvents, e.g. benzene or toluene, are employed.

The ketoesters prepared by process variant (a) ($R^3$ stands for an alkyl group having from 1 to 6 carbon atoms) can be converted into the corresponding ketocarboxylic acids by hydrolysis, preferably under alkaline conditions. The ketoesters and the corresponding ketocarboxylic acids can be decarboxylated by heating, under the usual conditions, to yield compounds of the formula (I), in which Z is a —$CH_2$— group.

The compounds of the formula (I), in which X stands for oxygen, can be converted into the corresponding compounds in which X represents an =$NR^4$ group ($R^4$ is as hereinabove defined) by means of well-known oxo-reactants. For example, the oxo-compounds can be converted into the corresponding oxime compounds with hydroxyl amine, while the corresponding imines can be obtained by reaction with ammonia.

In the compounds of formula (I) $R^1$ and/or $R^2$ can be converted into other substituents under the definition of $R^1$ and $R^2$, respectively. Thus, for example, from the compounds of formula (I), in which $R^1$ and/or $R^2$ is an alkoxy group having from 1 to 6 carbon atoms, the respective compounds in which $R^1$ and/or $R^2$ is hydroxyl can be prepared by desalkylation. Desalkylation can be carried out for example by heating with hydrogen bromide or iodide, or by means of anhydrous aluminium chloride. On the other hand, compounds of the formula (I) in which $R^1$ and/or $R^2$ is hydroxyl can be converted into the corresponding alkoxy derivatives by techniques known in the art. Methylation is preferably carried out with diazomethane or dimethyl sulfate, while the ethers with a longer carbon chain are obtained for example by the Williamson synthesis, using alkyl iodides.

Compounds of the formula (I) can be converted into their acid addition salts by reaction with suitable acids. Salt formation can be carried out, for example, in an inert organic solvent, such as a $C_{1-6}$ aliphatic alcohol, by dissolving the compound of the formula (I) in the solvent and adding the selected acid or a solution thereof formed with the same solvent to the first solution until it becomes slightly acidic. Thereafter the acid addition salt separates and can be removed from the reaction mixture e.g. by filtration.

The compounds of the formula (I) or the salts thereof can be subjected, if desired, to further purification, e.g. recrystallization. The solvents used for recrystallization are selected depending on the solubility and crystallization properties of the compound to be crystallized.

The new compounds of the formula (I) and their physiologically acceptable acid addition salts can be formulated for therapeutic purposes. The invention therefore relates also to pharmaceutical compositions comprising as active ingredient at least one compound of formula (I) or a physiologically acceptable salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, arabic gum, polyalkylene glycols, and vaseline (registered Trade Mark) can be used. The compounds can be formulated as conventional pharmaceutical formulations, for example in a solid (globular and angular pills, dragées, capsules, e.g. hard gelatine capsules) or liquid (injectable oily or aqueous solutions or suspensions) form. The quantity of the solid carrier can be varied within wide ranges, but preferably is between 25 mg and 1 g. The compositions optionally contain also conventional pharmaceutical additives, such as preserving agents, wetting agents, salts for adjusting the osmotic pressure, buffers, flavouring and aroma substances.

The compositions according to the invention optionally contain the compounds of formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For the pharmacological tests CFLP (LATI) mice of both sexes, weighing 18 to 22 g each, and male Han. Wistar (LATI) rats, weighing 160 to 180 g each, were used. The test materials were administered orally, in 30 mg/kg doses, in the form of a suspension containing 5% of Tween 80, one hour before the tests.

Test methods

1. Metrazole spasm (MET), mice

After pretreatment, the animals were administered 125 mg/kg of pentylenetetrazole subcutaneously. The animals which did not show a tonic extensoric spasm and survived the experiment were regarded protected. Observation time: one hour [Everett, L. M. and Richards, R. K.: J. Pharmacol. Exp. Ther. 81, 402 (1944)].

2. Analgesic activity (ANAL), mice

One hour after pretreatment, mice were administered 0.3 ml of a 0.6% acetic acid solution intraperitoneally, as a pain stimulus. The frequency of writhing syndrom was registered for 30 minutes. The changes observed as a result of treatment with the test compounds are related to the mean value of the frequency of writhing syndrom in the control group, and the difference is expressed in percentage [Koster, R. et al.: J. Pharmacol. Exp. Ther. 72, 74 (1941)].

3. Acute alcoholic intoxication (ETA), rats

One hour after pretreatment, the animals were administered 3.5 g/kg of ethyl alcohol, intraperitoneally. The narcosis time was registered, and the mean times of the individual test groups were related to the narcosis time of the control group. The difference is expressed in percentage.

The results of pharmacological test are set forth in Table I below.

Test compounds:
Compound "A": 1-(4'-oxo-cyclohexyl)-3,4-dihydro-6,7-dimethoxyisoquinoline,
Compound "B": 1-[(3'-methoxycarbonyl-4'-oxo)-1-cyclohexyl]-3,4-dihydro-6,7-dimethoxyisoquinoline

TABLE I

| Compound | MET | ANAL | ETA |
|----------|-----|------|-----|
| "A"      |     | −30% | −48% |
| "B"      | 40% |      | −55% |

The results show that both compounds substantially decrease the alcoholic narcosis time. In addition, compound "B" has a remarkable antispasm activity, while compound "A" has analgesic properties.

The invention is elucidated in more detail by the aid of the following non-limiting Examples.

EXAMPLE 1

4-[3,4-Dihydro-1(2H)-6,7-dimethoxyisoquinolinyl]-1,7-heptanedicarboxylic acid dimethyl or diethyl ester (compounds of formula (II))

82 g (0.4 mole) of 1-methyl-3,4-dihydro-6,7-dimethoxyisoquinoline are dissolved in 100 ml of benzene, 160 g (about 1.6 moles) of methyl or ethyl acrylate are added, and the mixture is refluxed for about 24 hours. The progress of the addition reaction is monitored by thin layer chromatography. The excess of methyl or ethyl acrylate and benzene are distilled off, and the residual brown oil is used in the next reaction step without further purification.

4-[3,4-dihydro-1(2H)-6,7-diethoxy-isoquinolinyl]-1,7-heptanedicarboxylic acid dimethyl or diethyl ester can be prepared in an analogous manner.

EXAMPLE 2

1-[3'-Methoxy- or Ethoxycarbonyl-4'-oxo)-1-cyclohexyl]-3,4-dihydro-6,7-dimethoxyisoquinoline The oily product obtained in Example 1 is dissolved in 500 ml of toluene, and the solution is poured into a 1-lit. flask containing sodium methylate evaporated to dryness. Dissolution is facilitated by moderate heating on a rotating evaporator. Simultaneously with dissolution precipitation of the sodium salt is observed. The pressure is carefully reduced in the equipment, and a portion of the solvent is evaporated under reduced pressure (30 mmHg). Toluene is supplemented, and the mixture is refluxed on an oil bath for 3 hours. Partial evaporation of the solvent and the addition of fresh solvent are repeated, and the mixture is refluxed for additional 6 hours.

The overwhelming part of toluene is distilled off, the mixture is acidified with a 25% aqueous hydrogen chloride solution under cooling, and after dissolution of the reaction product the remaining toluene is separated in a separating funnel. The aqueous part is decoloured with charcoal, filtered and alkalized with a saturated potassium carbonate solution. The crystals precipitated upon cooling are filtered off, washed with a small amount of water and subsequently ether, and dried. 76 g (91%) of the aimed product are obtained.

1-[(3'-Methoxy or -ethoxycarbonyl-4'-oxo)-1-cyclohexyl]-3,4-dihydro-6,7-diethoxyisoquinoline can be prepared in an analogous manner.

For the preparation of the hydrochlorides of the compounds obtained the bases are dissolved in absolute ethanol. To the solution absolute ethanol containing a one and a half-fold excess of dry hydrogen chloride gas is added. The mixture is evaporated, dissolved in a small amount of absolute ethanol, and hydrochloride is precipitated by addition of ether.

The physical and analytical data of the compounds prepared according to Example 2 are given in Table 1.

TABLE 1

1-[(3'-Methoxy- or ethoxycarbonyl-4'-oxo)-1-cyclohexyl]-3,4-dihydro-6,7-dimethoxyisoquinolines

[general formula (IA)] 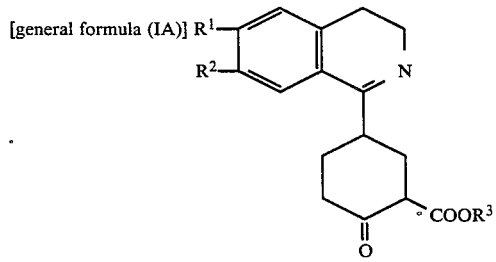

| $R^1 = R^2$ | $R^3$ | HX | Formula/mol. weight | Mp.: °C. Solvent | | Analysis, % calculated | found | Yield % |
|---|---|---|---|---|---|---|---|---|
| —OCH$_3$ | —CH$_3$ | — | C$_{19}$H$_{23}$NO$_5$ | 125–126 | C | 68.04 | 68.25 | 91 |
|          |         |   |                      |              | H | 6.91  | 7.18  |    |
|          |         |   | 335.39               | methanol/ether | N | 4.14  | 4.36  |    |
| —OCH$_3$ | —CH$_3$ | HCl | C$_{19}$H$_{24}$NO$_5$Cl | 200 | C | 59.76 | 59.50 | — |
|          |         |   |                      |              | H | 6.33  | 6.81  |    |
|          |         |   | 381.85               | methanol/ether | N | 3.65  | 3.75  |    |
|          |         |   |                      |              | Cl | 9.28  | 9.49  |    |
| —OCH$_3$ | —C$_2$H$_5$ | — | C$_{20}$H$_{25}$NO$_5$ | 103–105 | C | 66.83 | 67.28 | 83 |
|          |         |   |                      |              | H | 7.01  | 7.08  |    |
|          |         |   | 359.42               | ether        | N | 3.89  | 4.01  |    |
| —OCH$_3$ | —C$_2$H$_5$ | HCl | C$_{20}$H$_{26}$NO$_5$Cl | 213–214 | C | 60.67 | 60.75 | — |

TABLE 1-continued

1-[(3'-Methoxy- or ethoxycarbonyl-4'-oxo)-1-cyclohexyl]-
3,4-dihydro-6,7-dimethoxyisoquinolines

[general formula (IA)]

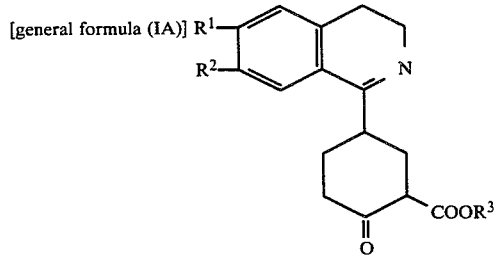

| $R^1 = R^2$ | $R^3$ | HX | Formula/ mol. weight | Mp.: °C. Solvent | Analysis, % calculated | found | Yield % |
|---|---|---|---|---|---|---|---|
| | | | 395.88 | ethanol | H 6.61 | 6.25 | |

EXAMPLE 3

1-(4'-Oxo-cyclohexyl)-3,4-dihydro-6,7-dimethoxyisoquinoline 16.7 g (0.05 mole) of 1-[(3'-methoxycarbonyl-4'-oxo)-1-cyclohexyl]-3,4-dihydro-6,7-dimethoxyisoquinoline are dissolved in 100 ml of 4n hydrochloric acid, and the mixture is slightly boiled for one hour until termination of carbon dioxide evolution. The mixture is then evaporated to dryness, the residue is dissolved in water, the solution is alkalized with ammonium hydroxide and the precipitated crystals are separated by filtration in vacuo and recrystallized from ether. Yield: 74%. Melting point: 103° to 105° C.

Analysis for $C_{17}H_{21}NO_3$ (287.36): calculated: C: 71.05%, H: 7.36%, N: 4.87%; found: C: 70.82%, H: 7.29%, N: 4.90%.

The hydrochloride prepared from the above base in a conventional manner with methanol containing an excess amount of hydrogen chloride gas, in a methanolic medium, melts at 207° to 208° C. (after crystallization from methanol/acetone).

Analysis for $C_{17}H_{22}NO_3Cl$ (323.87%): calculated: C: 63.05%, H: 6.84%, N: 4.32%; found: C: 62.67%, H: 6.21%, N: 4.45%.

EXAMPLE 4

4-[3,4-Dihydro-1(2H)-6,7-dimethoxyisoquinolinyl]-1,7-heptanedicarboxylic acid dinitrile (compound of formula (II))

A mixture of 23.3 g (0.1 mole) of 1-methyl-3,4-dihydro-6,7-dimethoxyisoquinoline, 100 ml of benzene and 26.5 ml (0.04 mole) of acryl nitrile is refluxed for about 50 hours. The progress of the reaction is monitored by thin layer chromatography. When the conversion is complete, benzene and acryl nitrile are distilled off, and the residue is recrystallized from methanol. After recrystallization the product melts at 106° C. Melting point of the corresponding hydrochloride, prepared by ethanolic solution of hydrochloric acid: 168° to 169° C. (after crystallization from ethanol). Yield: about 60%.

EXAMPLE 5

1-[(3'-Cyano-4'-imino)-1-cyclohexyl]-3,4-dihydro-6,7-dimethoxyisoquinoline 12.4 g (0.04 mole) of the dinitrile prepared in Example 4 are dissolved in 200 ml of toluene. To the solution 5.4 g (0.1 mole) of sodium methylate are added, and the mixture is refluxed for 50 hours. The progress of the reaction is monitored by thin layer chromatography. When the reaction is complete, the reaction mixture is allowed to cool to room temperature, acidified with cold dilute hydrochloric acid, and the aqueous phase is separated. The aqueous phase is then alkalized with sodium carbonate and extracted with chloroform several times. The combined chloroform phases are dried over anhydrous sodium sulfate and the solvent is evaporated in vacuo. The oily product obtained is converted into the corresponding hydrochloride with ethanolic hydrogen chloride, which is then crystallized from ethanol. Yield: about 30%. The hydrochloride melts at 255° C. (decomp.).

EXAMPLE 6

1-(4'-Cyclohexyloxime)-3,4-dihydro-6,7-dimethoxyisoquinoline 0.5 g of 1-(4'-oxo-cyclohexyl)-3,4-dihydro-6,7-dimethoxyisoquinoline [(I), X=O, Z=—CH$_2$—] and 0.5 g of hydroxylamine hydrochloride are suspended in 5 ml of ethanol, then 0.5 ml of pyridine are added to the suspension. The mixture is refluxed for 60 minutes, evaporated and diluted with water. After cooling the precipitated crystals are filtered off, washed and dried.

The aimed compound thus obtained melts at 192° C. Yield: 51%.

Analysis results: calculated: C: 67.52%, H: 7.33%, N: 9.26%; found: C: 68.49%, H: 7.41%, N: 10.11%.

EXAMPLE 7

1-{[3'-(Methoxycarbonyl)-4'-imino]-1-cyclohexyl}-3,4-dihydro-6,7-dimethoxyisoquinoline 6.68 g (0.02 mole) of 1-{[3'-(methoxycarbonyl)-4'-oxo]-1-cyclohexyl}-3,4-dihydro-6,7-dimethoxyisoquinoline are dissolved in 100 ml of a 28% solution of ammonia in methanol under moderate heating. The solution is allowed to stand at room temperature for two days, whereupon it is concentrated to half of its original volume under vacuum produced with a water pump (30 mmHg). The crystals precipitated upon cooling are filtered off. 5.5 g (80%) of the aimed compound are obtained, melting at 114° to 115° C.

Analysis for $C_{19}H_{23}N_2O_4$ (343.40): calculated: C: 66.45%, H: 6.75%, N: 8.50%; found: C: 66.15%, H: 6.92%, N: 8.26%.

We claim:

1. A 1-Cyclohexyl-3,4-dihydroisoquinoline derivative of the formula (I)

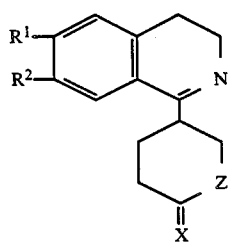

wherein
$R^1$ and $R^2$ each independently represents hydrogen, hydroxyl or alkoxy having from 1 to 6 carbon atoms,
X is oxygen and
Z is a =CH₂ or =CH—COOR³ group, in which $R^3$ is hydrogen or alkyl having from 1 to 6 carbon atoms; or
X represents an =NR⁴ group, in which $R^4$ is hydrogen or hydroxyl, and
Z is a =CH—CN, =CH₂ or =CH—COOR³ group, in which $R^3$ is as defined above, and an acid addition salt thereof.

2. A compound of the formula (I), in which $R^1$ and $R^2$ are both methoxy or ethoxy, while X, Z, $R^3$ and $R^4$ are as defined in claim 1.

3. A compound selected from the group consisting of
1-(4'-oxo-cyclohexyl)-3,4-dihydro-6,7-dimethoxyisoquinoline,
1-[(3'-methoxycarbonyl-4'-oxo)-1-cyclohexyl]-3,4-dihydro-6,7-dimethoxyisoquinoline,
1-[(3'-ethoxycarbonyl-4'-oxo)-1-cyclohexyl]-3,4-dihydro-6,7-dimethoxyisoquinoline,
1-[(3'-cyano-4'-imino)-1-cyclohexyl]-3,4-dihydro-6,7-dimethoxyisoquinoline,
1-(4'-cyclohexyloxime)-3,4-dihydro-6,7-dimethoxyisoquinoline,
1-{[3'-(methoxycarbonyl)-4'-imino]-1-cyclohexyl}-3,4-dihydro-6,7-dimethoxyisoquinoline
and hydrochlorides of these compounds.

4. A pharmaceutical composition comprising as an active ingredient an effective amount of at least one compound of the formula (I) of claim 1 or a physiologically acceptable salt thereof, in association with a pharmaceutical carrier and/or excipient.

5. A pharmaceutical composition comprising an effective amount of at least one compound as set forth in claim 3 or a hydrochloride thereof in association with a pharmaceutical carrier and/or excipient.

* * * * *